United States Patent
Vellinga et al.

(10) Patent No.: US 8,066,878 B2
(45) Date of Patent: Nov. 29, 2011

(54) ANAEROBIC PURIFICATION DEVICE

(75) Inventors: Sjoerd Hubertus Josef Vellinga, Tjalleberd (NL); Jelle Hendrik de Boer, Balk (NL); Antonius Johannes Jorna, Balk (NL); Leonard Hubertus Alphonsus Habets, Sneek (NL)

(73) Assignee: Paques B.V. (NL)

( * ) Notice: Subject to any disclaimer, the term of this patent is extended or adjusted under 35 U.S.C. 154(b) by 418 days.

(21) Appl. No.: 11/919,410

(22) PCT Filed: Jun. 10, 2005

(86) PCT No.: PCT/NL2005/000423
§ 371 (c)(1),
(2), (4) Date: Aug. 7, 2009

(87) PCT Pub. No.: WO2006/132523
PCT Pub. Date: Dec. 14, 2006

(65) Prior Publication Data
US 2009/0308806 A1    Dec. 17, 2009

(51) Int. Cl.
*C02F 3/28* (2006.01)
(52) U.S. Cl. ........................ 210/603; 210/188
(58) Field of Classification Search ............ 210/603, 210/188
See application file for complete search history.

(56) References Cited

U.S. PATENT DOCUMENTS

| | | | |
|---|---|---|---|
| 4,632,692 A * | 12/1986 | Lebesgue et al. | 71/10 |
| 6,063,273 A | 5/2000 | Habets et al. | |
| 6,602,416 B1 | 8/2003 | Rossmanith | |
| 2002/0000409 A1 * | 1/2002 | Lanting et al. | 210/603 |
| 2003/0085171 A1 | 5/2003 | Khudenko | |

FOREIGN PATENT DOCUMENTS

| | | |
|---|---|---|
| EP | 170332 | 2/1986 |
| JP | 7-204682 A * | 8/1995 |
| WO | 92/01637 | 2/1992 |

* cited by examiner

*Primary Examiner* — Fred Prince
(74) *Attorney, Agent, or Firm* — The Webb Law Firm

(57) ABSTRACT

The invention relates to an anaerobic purification device for purification of influent. The device has a reactor tank, an inlet for introducing influent into the tank, a water collecting device for collecting purified water, a gas collecting system for collecting gas from the fluid contained in the reactor, a gas-liquid separation device, a riser for passing liquid into the separation device by gas lifting action caused by gas collected in the gas collecting system, and a downer for returning liquid and sludge from the separation device into the lower tank section. According to the invention this device is characterized in that it is arranged to define, in the downer at the level of the liquid surface, a head pressure of, at least, approximately 1.4 m water column (approximately 0.14 bar). The invention also relates to a method for anaerobic purification device for purification of influent.

19 Claims, 3 Drawing Sheets

ANAEROBIC PURIFICATION DEVICE

BACKGROUND OF THE INVENTION

1) Field of the Invention

The present invention relates to an anaerobic purification device for purification of influent, such as wastewater, the anaerobic purification device comprising:

a reactor tank;

inlet means for introducing influent into the tank, the inlet means being located in the lower section of the tank;

water collecting means, such as an overflow gutter, for collecting purified water, the water collecting means being provided at the upper section of the tank and defining a liquid surface in said reactor tank;

at least one gas collecting system for collecting gas from the fluid contained in the reactor, the at least one gas collecting system being arranged at a level below the water collecting means;

a gas-liquid separation device arranged at a level above the water collecting means;

at least one riser having a discharge opening debouching into the separation device, the at least one riser being connected to the at least one gas collecting system for raising fluid contained in the tank by gas lift action caused by gas collected in the at least one gas collection system;

a downer having an inlet debouching into the separation device and an outlet debouching in the lower section of the tank for returning liquid separated in the separation device, into the lower section of the tank.

2) Description of Related Art

Such a device is known from EP-A-170.332. According to this EP-A-170.332 one subjects wastewater that contains organic material to a process in which dissolved organic material is broken down under anaerobic conditions. By contact with biomass that contains methane-producing microorganisms, methane is being produced which is separated from the liquid. The treated water (effluent) is removed via overflows weirs. EP-A-170.332 describes as starting point for that invention on page 1 lines 21-32: It has been found that with a residence time of several hours a purification of as much as 90% can be reached. The extent to which such purification efficiency can be maintained over a long period also depends on the sludge retention In particular, care must be taken to ensure that on average no more sludge is rinsed out of the reactor than can be formed in a certain period of time. If a high hydraulic flow is used with a low COD concentration in the influent, there is a considerable risk that the internal settler will not be capable of preventing a large amount of sludge being flushed out. A factor which is of importance in this connection is the hydraulic surface loading of the settler. In the subsequent passage, EP-A-170.332 explains that the upward flowing water and the rising gas bubbles can stir up the biomass flocks and particles considerably. These can arrive into the uppermost part of the reactor where the gas collecting system is located. The turbulence produced can thus result in excessive quantities of biomass to be flushed out of the reactor. This limits the loading capacity of the reactor considerably.

The invention of EP 170 332 aims to overcome the disadvantages just described and to create a reactor in which the main gas load is taken away from an uppermost gas collecting system. For this purpose EP 170 332 provides at least one additional gas collecting system for collecting gas, which additional system is arranged at a distance below the upper collecting system. The additional system has a hydraulic link with at least one riser pipe for raising liquid by gas lift action, said riser pipe discharging into at least one separation device for separating gas and liquid. In view of the fact that gas is trapped at a considerable distance below the liquid level and is conveyed further via the riser pipe, an essentially turbulence-free flow can occur in the upper section of the reactor. This increases the loading capacity, whereas at the top, clean effluent is obtained. It is important that the liquid, which is carried along with the gas to the riser pipe, is separated and returned to the reactor: While a quiet, eddy-free flow is required at the top of the reactor, very good mixing of sludge and fluid is required at the bottom of the reactor. For this purpose the heavy sludge near the bottom has to be fluidized. In a preferred embodiment according to EP 170 332 this fluidization can be achieved in the bottom section of the reactor with the aid of energy obtained from the gas lifting liquid in the riser pipe. The lifted liquid is separated from the gas and, under influence of hydraulic gravity pressure, returned from the separation device, through a downer pipe, to the bottom section of the reactor chamber.

For economic reasons, it is becoming more and more interesting to make the reactor column as high as possible. In that case, there would be more reactor volume and more biomass, whereas the footprint—the square meters of surface area occupied by the reactor—is the same. On the other hand, the higher the reactor the heavier the column of biomass in the reactor will be. The heavier the column of biomass, the more difficult it will be to maintain a good mixing and fluidization pattern near the bottom of the reactor. In some cases it may also happen that the biomass mixture becomes heavier due to the precipitation of inorganic material. Also in that case, it can be difficult to maintain a good fluidization.

A solution could be increasing the head pressure. However, prior art and experience teaches that, for a good mixture at the bottom of the reactor and overall functioning of the reactor, one requires, at the level of the liquid surface in the reactor, a head pressure of about 0.8 to 1 m water column (i.e. about 0.08-0.1 bar) in the downer, in order to overcome the pressure loss, which is required for good distribution at the bottom in the sludge bed. Too low head pressures result in non-optimal mixing at the bottom of the reactor and/or a poorer performance of the reactor respectively the 'process carried out in the reactor' as a whole, whereas too high head pressure would result in very high shear forces on the biomass particles, and consequently destruction of the granular material.

In practice at least about 80% of the head pressure is obtained from hydraulic pressure, whilst at most about 20% of the head pressure is obtained from gas pressure resulting from gas load situations during use. However in particular cases this has lead to problems with fluidization of the sludge in the bottom of the reactor and/or quite irregular gas flows.

Thus although for economic reasons one would like to make the reactor column as high as possible, the reactor height is in practice limited, because of the effects and teaching just mentioned.

SUMMARY OF THE INVENTION

The present invention has the objective to provide an anaerobic purification device for purification of influent, such as wastewater, with improved fluidization at the bottom of the reactor which also allows increasing the reactor height.

According to the invention this object is achieved by providing an anaerobic purification device for purification of influent, such as waste water, the anaerobic purification device comprising:

a reactor tank;

inlet means for introducing influent into the tank, the inlet means being located in the lower section of the tank;

water collecting means, such as an overflow gutter, for collecting purified water, the water collecting means being provided at the upper section of the tank and defining a liquid surface in said reactor tank;

at least one gas collecting system for collecting gas from the fluid contained in the reactor, the at least one gas collecting system being arranged at a level below the water collecting means;

a gas-liquid separation device arranged at a level above the water collecting means;

at least one riser having a discharge opening debouching into the separation device, the at least one riser being connected to the at least one gas collecting system for raising fluid contained in the tank by gas lift action caused by gas collected in the at least one gas collection system;

a downer having an inlet debouching into the separation device and an outlet debouching in the lower section of the tank for returning liquid separated in the separation device, into the lower section of the tank;

characterized in that the purification device is arranged to define, in the downer at the level of the liquid surface, a head pressure of at least about 1.4 m (m stands for meter) water column (about 0.14 bar).

In this respect, the head pressure is defined as the difference in pressure, at the level of the liquid surface in the reactor (which level is defined by the water collecting means, such as an overflow gutter), between a point inside the downer and a point outside the downer but inside the tank.

According to a preferred embodiment of the invention, the head pressure is at least about 1.5 m water column (about 0.15 bar), preferably at least about 1.6 m water column (0.16 bar).

According to a further preferred embodiment of the invention, the head pressure is at least 1.8-2 m water column (about 0.18-0.2 bar), such as 2.5-3 m water column (0.25-0.3 bar) or more.

The invention as well as the above both advantageous embodiments will be explained below, as well as several further embodiments of the invention.

According to the invention solutions have been found to create more head pressure without decreasing the performance of the reactor as might have been expected, but instead increase of performance came within reach.

The reactor can, according to the invention, be designed in such manner that the device itself defines a head pressure of at least about 1.4 m water column, i.e. in use the head pressure will be at least 1.4 meter water column due to structural features present in the device. According to the invention there are several solutions each involving there own structural features.

A first solution is to place the gas-liquid separation device at a higher level above the reactor tank in order to allow for more hydraulic pressure. As a consequence, not only that part of the riser pipe extending above the liquid surface needs to be extended but also the driving force of the gas for lifting water column to the gas-liquid-separation device. This can be done, for example, by increasing the length of the riser extending below the water surface, and/or by decreasing the flow resistance of the riser—for example by changing the diameter of the pipe—. Lowering the position where the gas is introduced into the riser creates more driving force for lifting the water column to the separation device. The upward pressure created by the displaced water volume in the riser pipe generates the driving force to bring the water to the gas-liquid separation device.

A preferred embodiment according to this first solution is characterized in that the at least one riser (5) has a top part (26) which is defined as that part of the riser (5) extending upwards as from said liquid surface (21), and wherein said top part has a length (H3) which is at least about 1.2 m, preferably at least about 1.4 m, such as 1.6-2 m or more.

A second solution is to operate at a higher gas pressure in the gas-liquid separator. This second solution can be achieved, for example, by arranging the gas-liquid-separating process in an essentially closed vessel provided with means for keeping the gas pressure at predetermined threshold value. In this way an extra head pressure of 0.3 to 1.0 m water column can be gained or even more if required. According to a preferred embodiment of this second solution, said threshold value is at least about 0.25 m water column (about 0.025 bar), such as at least about 0.5 m water column (about 0.05 bar). According to another preferred embodiment of this second solution, said threshold value is at most about 1.5 m water column (about 0.15 bar), such as at most about 1.2 m water column (about 0.12 bar).

A third solution is improving the flow of fluid flowing through the downer. This can, for example, be achieved by providing means that allow the fluid to enter the downer continuously and easily. According to an embodiment of this third solution, the gas-liquid-separation device comprises a vessel, wherein the inlet of the downer is conically shaped with respect to a vertical axis and with the taper in the downward direction, and wherein the discharge opening of the at least one riser is arranged to create a tangential fluid flow in the vessel around the conically shaped inlet of the downer.

A fourth solution is a combination of one or more of the three afore mentioned solutions or possible other solutions.

An important factor of influence is the quantity of gas production in the reactor, which is a result of the applied COD loading and the COD conversion rate. A higher gas production per specific reactor surface (for instance expressed in m3gas/m2.h) causes a stronger gas lift, whereas at a lower gas production, the gas lift will slow down and will finally stop. As higher reactor columns will theoretically produce more m3gas/m2.h, the extra driving forces for more internal circulation flow or for lifting the water to a higher gas-liquid separation device will be available. Applicant found, contrary to what was expected, that this additionally available driving force is of an amount substantially enough to allow, contrary to prevailing prejudices, an increase of head pressure by simple design measures in the anaerobic purification device.

Since the reactors can be operated in a very wide range of Volumetric Loading Rates (VLR), in general between 5 and 35 kg COD/m3.d, the correct dimensioning should take into account the most probable operational circumstances.

Now that for economic reasons, reactors higher than 20 m more often will to be constructed, it has been found that the internal circulation can be maintained or even improved by taking specific measures. Considering that the density of the biomass sludge is higher than water, that the downer pipe as well as the inlet distribution system causes a pressure loss and that the sludge bed has a certain resistance against fluidization, it has been found that for a "normal" gas pressure of 20 to 30 cm Water Column, the gas lift needs to bring the water to a level of at least 1.2 m above the water level in the reactor, preferably 1.4 to 1.6 m and in some cases even above 2.2 m. In order to accommodate this for average reactor loads between 15 and 30 kg COD/m3.d, the total length of the riser pipe needs to be chosen such that the top part of the riser extending upwards as from said liquid surface—i.e. the length above the water collecting means, such as the overflow gutter—will be between at least about 10%, such as at least about 15%, and/or at most about 30%, such as at most about 25%, of the total length of the riser pipe. Alternatively, the gas pressure could be increased to 60 or 70 cm water column or even above 1.0 m water column. Also combinations of the two measures are possible, for instance raising the water column by the gas lift to 1.6 m and increasing the gas pressure to 60 cm water column in order to make a combined pressure or head pressure of 2.2 m water column. Taking these measures into account, reactor heights could be realized in the range of 24 to 36 m or even higher.

According to an advantageous embodiment of the invention, the device further comprises upper gas collecting means (10) for collecting and removing gas from the fluid contained in the tank (14), the upper gas collecting means (10) being provided between the water collecting means (11) and the at least one gas collecting system (4).

The present invention is also embodied by, and thus relates to, the use of an anaerobic purification device according to the invention.

The present invention is also embodied by, and thus relates to, a method of operating an anaerobic purification device for purification of influent, such as waste water, the anaerobic purification device comprising:

a reactor tank;

inlet means for introducing influent into the tank, the inlet means being located in the lower section of the tank;

water collecting means, such as an overflow gutter, for collecting purified water, the water collecting means being provided at the upper section of the tank and defining a liquid surface in said reactor tank;

at least one gas collecting system for collecting gas from the fluid contained in the reactor, the at least one gas collecting system being arranged at a level below the water collecting means;

a gas-liquid separation device arranged at a level above the water collecting means;

at least one riser having a discharge opening debouching into the separation device, the at least one riser being connected to the at least one gas collecting system for raising fluid contained in the tank by gas lift action caused by gas collected in the at least one gas collection system;

a downer having an inlet debouching into the separation device and an outlet debouching in the lower section of the tank for returning liquid separated in the separation device, into the lower section of the tank;

characterized in that
the anaerobic purification device is operated with a head pressure of at least about 1.4 m water column (about 0.14 bar), said head pressure prevailing in the downer at the level of the liquid surface.

Advantages of the use according to the invention as well as the method according to the invention and its preferred embodiments according to claims 14-17, will be clear from the preceding explanation in relation to the device according to the invention.

BRIEF DESCRIPTION OF THE DRAWINGS

In the next following the present invention will be further elucidated with reference to a drawing. In this drawing.

DETAILED DESCRIPTION OF THE INVENTION

Figure 1:
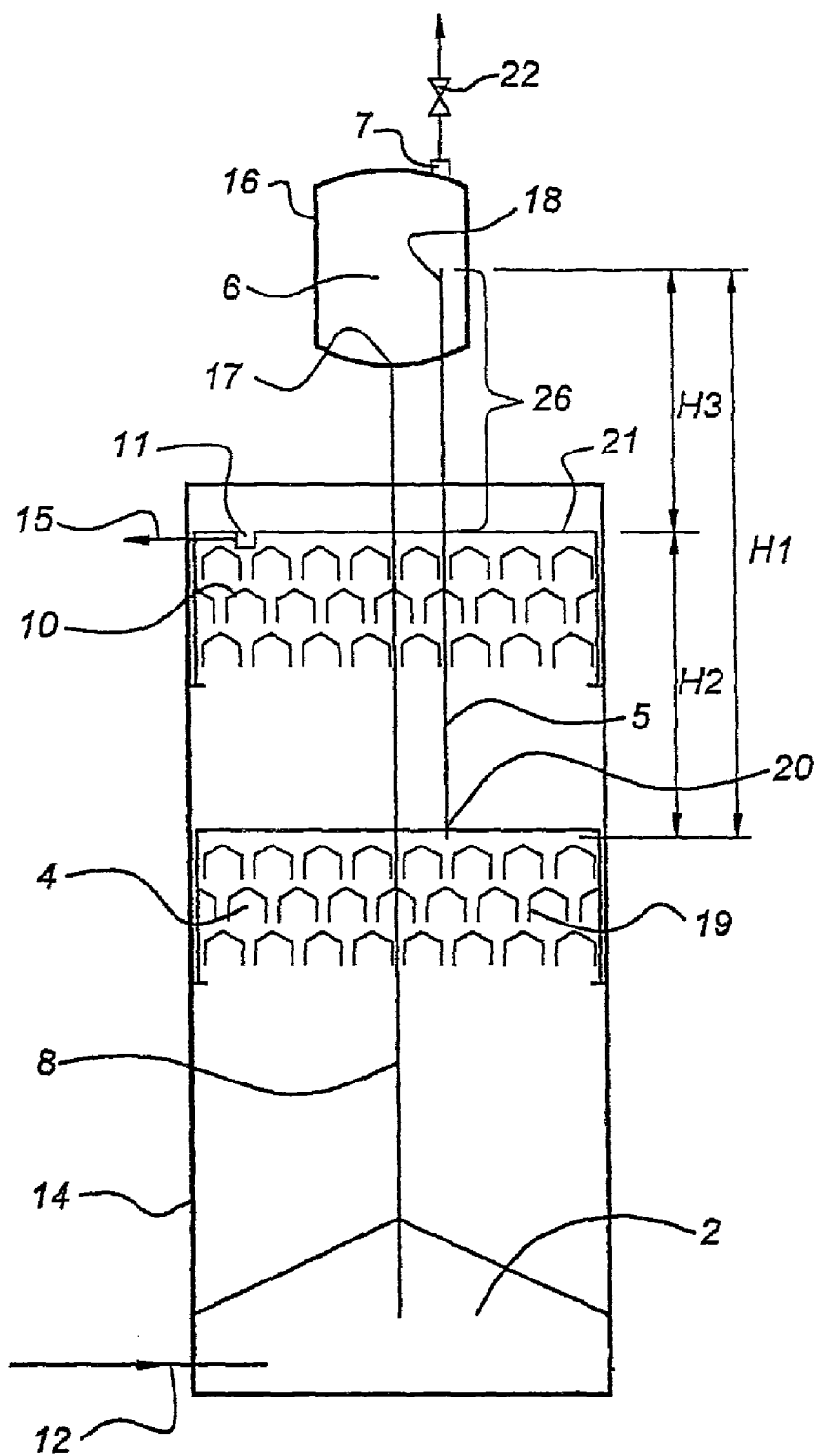
FIG. 1 shows very schematically an anaerobic purification device according to the invention.

The anaerobic purification equipment shown in FIG. 1 comprises a tall container 14, called reactor tank.

In the bottom end of the reactor tank 14, there is provided a mixing zone 2 for influent introduced via supply 12. As the skilled man knows, such a mixing zone 2 can be accomplished in several ways. One advantageous manner of accomplishing the mixing zone is providing an inlet system in accordance with WO 92/01637.

In the upper part of the reactor tank, water-collecting means in the form of overflow gutters 11 or other means are fitted which are connected to an effluent drainpipe 15 for discharging purified effluent. The water-collecting means define the level of the liquid surface 21 in the reactor tank 14. In case of overflow gutters 11, this level of the liquid surface 21 will be determined by the overflow edge of said gutters 11.

Within the reactor tank 14 two gas-collecting arrangements 4 and 10 for collecting and removing gas are fitted. Each of the gas collecting arrangements comprises a multiplicity of hoods 19. Per gas collecting arrangement the hoods can be arranged in one layer or several layers, such as three layers as shown in the figure. Number 10 is, especially in the claims, called the upper gas collecting means and 4 is called, especially in the claims, the at least one gas collecting system. FIG. 1 shows only one gas collecting system 4, but within the framework of the invention also two, three or more gas collection systems could be provided. The upper gas collecting means 10 need not to be connected to the riser 5 and might be absent in case the fluid at this height of the tank is gas poor, or might be discharged separately to the gas liquid-separation device 6 or elsewhere.

Above the reactor there is provided a gas-liquid separation device 6. This gas-liquid separation device comprises an essentially closed vessel 16—although also an open vessel is possible, see FIG. 2—having a gas outlet 7 for discharging gas such as biogas, a liquid outlet 17, and an inlet 18 for supplying a fluid containing the gas and liquid to be separated. The liquid outlet 17 is the upper end of a downer pipe 8, or said differently the inlet of downer 8. The inlet 18 is the upper end of a riser pipe 5, or said differently the discharge opening of the riser. The gas outlet 7 is optionally provided with means 22, for keeping the gas pressure in the vessel at a predetermined threshold value. Preferably the threshold value will have a minimum value of about 0.25 m water column (about 0.025 bar). Optionally the threshold value can have a maximum value of about 1.5 m water column (about 0.15 bar).

The riser 5 has a lower end with an inlet for drawing in fluid. This fluid is drawn in by gas lift action caused by gas collected by the at least one gas collection system 4 (lower level separators). For this purpose the hoods 19 of the at least one gas collection system 4 are connected to the riser in such a way, that the collected gas creates the gas lift in the riser. As such all this concerning the riser is known from the prior art and can, as the skilled man knows, be realized in several manners.

The downer 8 extends from the gas-liquid separation device 6 to the bottom region of the tank 14. Under the influence of gravity, liquid from the separation device, which can—depending from where the biomass is located—contain biomass as well is returned to the bottom of the tank. At the bottom of the tank this return flow causes fluidization of the bed of biomass.

Figure 2A:
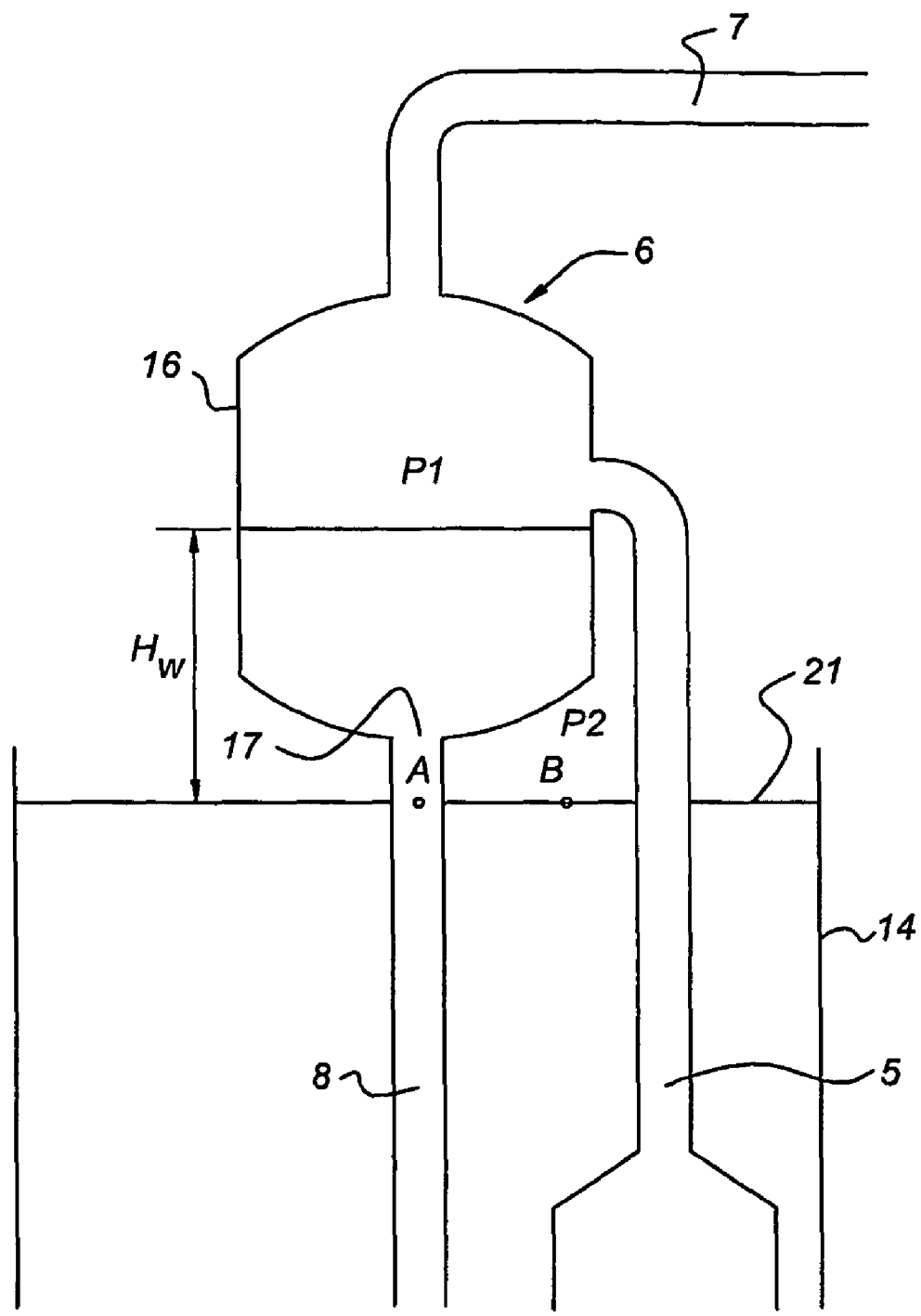
FIGS. 2A en 2B show schematically a part of purification devices according to the invention to explain the term "head pressure".
Figure 2B:
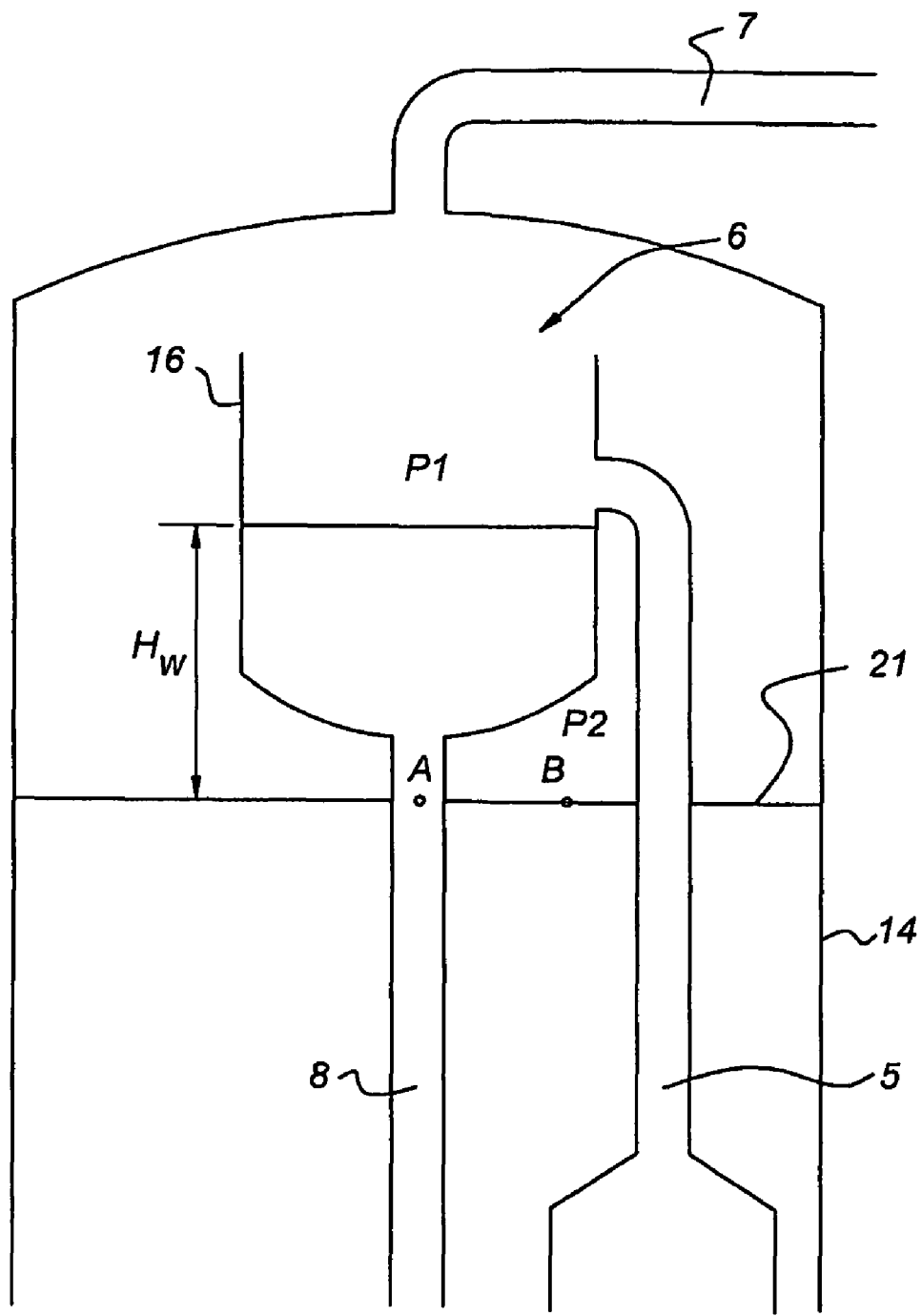

FIGS. 2A and 2B show highly schematically two different embodiments according to the invention, with the purpose to explain the term head pressure as used in this application. For corresponding parts, we used the same reference numbers as with respect to FIG. 1.

In both FIGS. 2A and 2B the head pressure $P_{head}$ is the pressure difference between points A and B. Point A, having the pressure $P_A$, lies inside the downer 8 at the level of the liquid surface 21 in the tank 14. Point B, having the pressure $P_B$, lies outside the downer, but inside the reactor at the same level of the liquid surface. The pressure caused by the water column $H_W$ above the point A is called $P_W$. The pressure $P_1$ is the gas pressure just above the liquid level in the gas-liquid-separation device 6. $P_2$ is the gas pressure just above the liquid level 21 in the reactor tank. All pressures are measured relative to the atmospheric pressure.

In the embodiment according to FIG. 2A, the gas-liquid-separation device 6 comprises a closed vessel 16. In this closed vessel the gas pressure is $P_1$. The reactor tank 14 has a so called open top. This means the top communicates with the environment so that the gas pressure $P_2$ in the top of the reactor is about the atmospheric pressure; thus about zero/relative to atmospheric pressure. However, the reactor tank can also have a closed top allowing the gas pressure $P_2$ to be different from the atmospheric pressure. Here for the head pressure applies:

$$P_{head} = P_A - P_B = P_W + P_1 - P_2$$

In the embodiment according to FIG. 2B, the gas-liquid-separation device 6 has an open top and the reactor tank 14 has a closed top. Further the gas-liquid-separation device is arranged inside the reactor tank 14. Consequently the pressures $P_1$ and $P_2$ are identical. Here for the head pressure applies:

$$P_{head} = P_A - P_B = P_W + P_1 - P_1 = P_W$$

In FIG. 2B, the head pressure would be the same when also the reactor tank 14 is an open tank.

During operation, fermentation takes place under anaerobic conditions as a result of contact between sludge granules or biomass flocks and substances soluble in water, such as fatty acids, methane being formed. In order to achieve a quiet, turbulence-free flow in the uppermost part of the reactor and to ensure that virtually no sludge is carried off with the effluent, the additional gas collecting means 4 are provided at a level, which is at a substantial distance below the overflow gutters 11. In separator 6 liquid and gas are separated from each other by gravity and the liquid gathers at the bottom section of the separator and is—as explained above—returned into the mixing zone 2 of the reactor tank via the downer 8 to support the mixing.

As a result of the fact that the gas has lifted the water well above the fluid in the reactor tank 14, the liquid column in the downer 8 produces a fairly powerful downward flow in the downer pipe 8, which provides extra mixing at the bottom of the reactor. In a simple way the effect is therefore achieved that tranquility prevails at the top of the reactor and heavy sludge and influent at the bottom of the reactor are thoroughly mixed by turbulence.

In the Figures, number 20 indicates the position at which the gas—collected by the additional gas collection system—is introduced into the riser, H2 indicates the vertical distance between said gas introduction point 20 and the level of the water collection means 11 (effluent weirs/gutters), which level is in fact the fluid level 21 in the tank H3 indicates the vertical distance between the discharge opening 18 of the riser 5 and the level of the water collection means. H1 is essentially the sum of H2 and H3, i.e. H1=H2+H3. The length of H3 can be in the range of 10% to 30% of H1. The discharge opening of the riser(s) 18 is preferably located above the fluid level in the gas-liquid separator and designed in a way to create a tangential flow pattern in the gas-liquid separator device 6 for optimizing the separation process. The inlet opening to the downer pipe 8 is preferably conically shaped to avoid gas entrapment and enable a constant downward flow.

Within the scope of the invention various modifications are possible. The embodiments drawn and described are only examples. All the embodiments have in common that a significant portion of the gas evolved during the fermentation is collected before it can reach the uppermost section of the reactor and that the liquid propelled up in this process by the gas-lifting action is separated from gas and the potential energy of the relatively heavy liquid column is used via a re-circulating flow to obtain the stirring necessary for a thorough mixing and fluidization at the bottom of the reactor. Power which would have been released at the top of the reactor is now taken to the bottom. The load capacity of the reactor is considerably increased as a result of the tranquillity at the top near the water outlet and the turbulence at the bottom near the water inlet.

The invention claimed is:

1. An anaerobic purification device for purification of influent fluid, the anaerobic purification device comprising:
   a) a reactor tank;
   b) an influent inlet for introducing influent fluid into the tank, the influent inlet being located in a lower section of the tank;
   c) a water collecting device for collecting purified water, the water collecting device being provided at an upper section of the tank and defining a liquid surface in the reactor tank;
   d) at least one gas collecting system for collecting gas from the fluid contained in the reactor tank, the at least one gas collecting system being arranged at a level below the water collecting device;
   e) a gas-liquid separation device arranged at a level above the water collecting device;
   f) at least one riser having a discharge opening debouching into the separation device, the at least one riser being connected to the at least one gas collecting system for raising fluid contained in the tank by gas lift action caused by gas collected in the at least one gas collection system; and
   g) a downer having a downer inlet commencing into the separation device and a downer outlet debouching in the lower section of the tank for returning liquid separated in the separation device, into the lower section of the tank;
   wherein the purification device is arranged to define, in the downer at the level of the liquid surface, a head pressure of, at least, approximately 1.4 m water column (approximately 0.14 bar), and
   wherein the at least one riser has a top part, which is defined as that part of the riser extending upwards from the liquid surface, and wherein the top part has a length which is, at least, approximately 1.2 m.

2. The anaerobic purification device according to claim 1, wherein the head pressure is, at least, approximately 1.5 m water column (approximately 0.15 bar).

3. The anaerobic purification device according to claim 1, wherein the head pressure is, at least, approximately 1.8 m water column (approximately 0.18 bar).

4. The anaerobic purification device according to claim 1, wherein the top part has a length which is, at least, approximately 10% of a total length of the at least one riser.

5. The anaerobic purification device according to claim 1, wherein the top part has a length which is, at most, approximately 30% of a total length of the at least one riser.

6. The anaerobic purification device according to claim 1, wherein the gas-liquid separation device comprises an essentially closed vessel provided with a keeping device for keeping a gas pressure at a threshold value.

7. The anaerobic purification device according to claim 6, wherein the threshold value is, at most, approximately 1.5 m water column (approximately 0.15 bar).

8. The anaerobic purification device according to claim 6, wherein the threshold value is, at least, approximately 0.25 m water column (approximately 0.025 bar).

9. The anaerobic purification device according to claim 8, wherein the threshold value is, at most, approximately 1.5 m water column (approximately 0.15 bar).

10. The anaerobic purification device according to claim 1, wherein the gas-liquid-separation device comprises a vessel, wherein the downer inlet is conically shaped with respect to a vertical axis and with a taper in a downward direction, wherein the conically shaped downer inlet is arranged inside the vessel, and wherein the discharge opening of the at least one riser is arranged to create a tangential fluid flow in the vessel around the conically shaped downer inlet.

11. The anaerobic purification device according to claim 1, wherein the purification device further comprises an upper gas collecting device for collecting and removing gas from the fluid contained in the tank, the upper gas collecting device being provided between the water collecting device and the at least one gas collecting system.

12. The anaerobic purification device according to claim 1, wherein the influent fluid is waste water.

13. The anaerobic purification device according to claim 1, wherein the water collecting device is an overflow gutter.

14. A method of operating an anaerobic purification device for purification of influent fluid, comprising the steps of:
   a) providing a reactor tank;
   b) providing an influent inlet, the influent inlet being located in the lower section of the tank;
   c) providing a water collecting device at an upper section of the tank;
   d) providing at least one gas collecting system at a level below the water collecting device;
   e) providing a gas-liquid separation device at a level above the water collecting device;
   f) providing at least one riser having a discharge opening debouching into the separation device, the at least one riser being connected to the at least one gas collecting system, wherein the at least one riser has a top part, which is defined as that part of the riser extending upwards from the liquid surface, and wherein the top part has a length which is, at least, approximately 1.2 m;
   g) providing a downer having a downer inlet commencing into the separation device and a downer outlet debouching into the lower section of the tank;
   h) introducing influent fluid into the tank via the influent inlet;
   i) collecting purified water in the water collecting device;
   j) defining a liquid surface in the reactor tank with the water collecting device;
   k) collecting gas from the fluid container in the reactor tank with the at least one gas collecting system;
   l) raising fluid contained in the tank by gas lift action within the at least one riser, the gas lift action being caused by gas collected in the at least one gas collection system;
   m) separating fluid in the gas-liquid separation device;
   n) returning separated liquid into the lower section of the tank via the downer outlet; and
   o) operating the anaerobic purification device with a head pressure of, at least, approximately 1.4 m water column (approximately 0.14 bar), the head pressure prevailing in the downer at the level of the liquid surface.

15. The method according to claim 14, wherein the head pressure is, at least, approximately 1.5 m water column (approximately 0.15 bar).

16. The method according to claim 14, wherein the head pressure is, at least, approximately 1.8 m water column (approximately 0.18 bar).

17. The method according to claim 14, wherein the gas-liquid separator device comprises an essentially closed vessel, and wherein a gas pressure prevailing in the vessel is, at least, approximately 0.3 m water column (approximately 0.03 bar).

18. The method according to claim 17, wherein the gas pressure prevailing in the vessel is, at most, approximately 1.5 m water column (approximately 0.15 bar).

19. The method according to claim 14, wherein the influent fluid is waste water.

* * * * *